(12) United States Patent
Terai

(10) Patent No.: US 8,596,262 B2
(45) Date of Patent: *Dec. 3, 2013

(54) LIQUID DISCHARGE HEAD AND LIQUID DISCHARGE HEAD DEVICE

(75) Inventor: Haruhiko Terai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 669 days.

This patent is subject to a terminal disclaimer.

(21) Appl. No.: 12/763,976

(22) Filed: Apr. 20, 2010

(65) Prior Publication Data

US 2010/0269823 A1 Oct. 28, 2010

(30) Foreign Application Priority Data

Apr. 24, 2009 (JP) .................................. 2009-106254

(51) Int. Cl.
*A61M 16/18* (2006.01)
*A61M 11/00* (2006.01)
*B05B 17/04* (2006.01)

(52) U.S. Cl.
USPC ............ 128/200.16; 128/200.14; 128/200.24; 128/203.12; 128/203.15

(58) Field of Classification Search
USPC ............ 128/200.11–200.24, 203.12, 203.15, 128/203.19, 203.21; 222/55; 239/102.1, 239/102.2; 347/44, 47, 56, 63, 64, 67; 216/2, 27, 57, 79

See application file for complete search history.

(56) References Cited

U.S. PATENT DOCUMENTS

| | | | | |
|---|---|---|---|---|
| 5,659,343 A * | 8/1997 | Koizumi et al. | ................. | 347/47 |
| 6,830,046 B2 * | 12/2004 | Blakley et al. | ........... | 128/200.14 |
| 7,581,809 B2 * | 9/2009 | Eguchi et al. | .................... | 347/20 |
| 7,726,303 B2 * | 6/2010 | Tyvoll et al. | ............. | 128/200.21 |
| 7,744,192 B2 * | 6/2010 | Lu | .................... | 347/44 |
| 2004/0125175 A1 * | 7/2004 | Yang et al. | ...................... | 347/65 |
| 2005/0150489 A1 * | 7/2005 | Dunfield et al. | ......... | 128/200.14 |
| 2010/0288270 A1 * | 11/2010 | Wada et al. | .............. | 128/200.14 |

FOREIGN PATENT DOCUMENTS

| | | |
|---|---|---|
| JP | 2001-105584 | 4/2001 |
| JP | 2003-154655 | 5/2003 |
| JP | 2004-001439 | 1/2004 |

* cited by examiner

*Primary Examiner* — Annette Dixon
(74) *Attorney, Agent, or Firm* — Canon USA Inc IP Division

(57) ABSTRACT

A liquid discharge head includes an energy generating element which generates energy to be used to discharge a liquid; and a plurality of discharge ports which is formed for each energy generating element and allows the liquid to be discharged therethrough. The plurality of discharge ports have regions where the angles of contact with the liquid are different around the discharge ports, and the regions in the discharge ports where the contact angles are relatively small are formed at different positions in the plurality of discharge ports, and the liquids discharged from the plurality of discharge ports are discharged in directions away from each other.

5 Claims, 5 Drawing Sheets

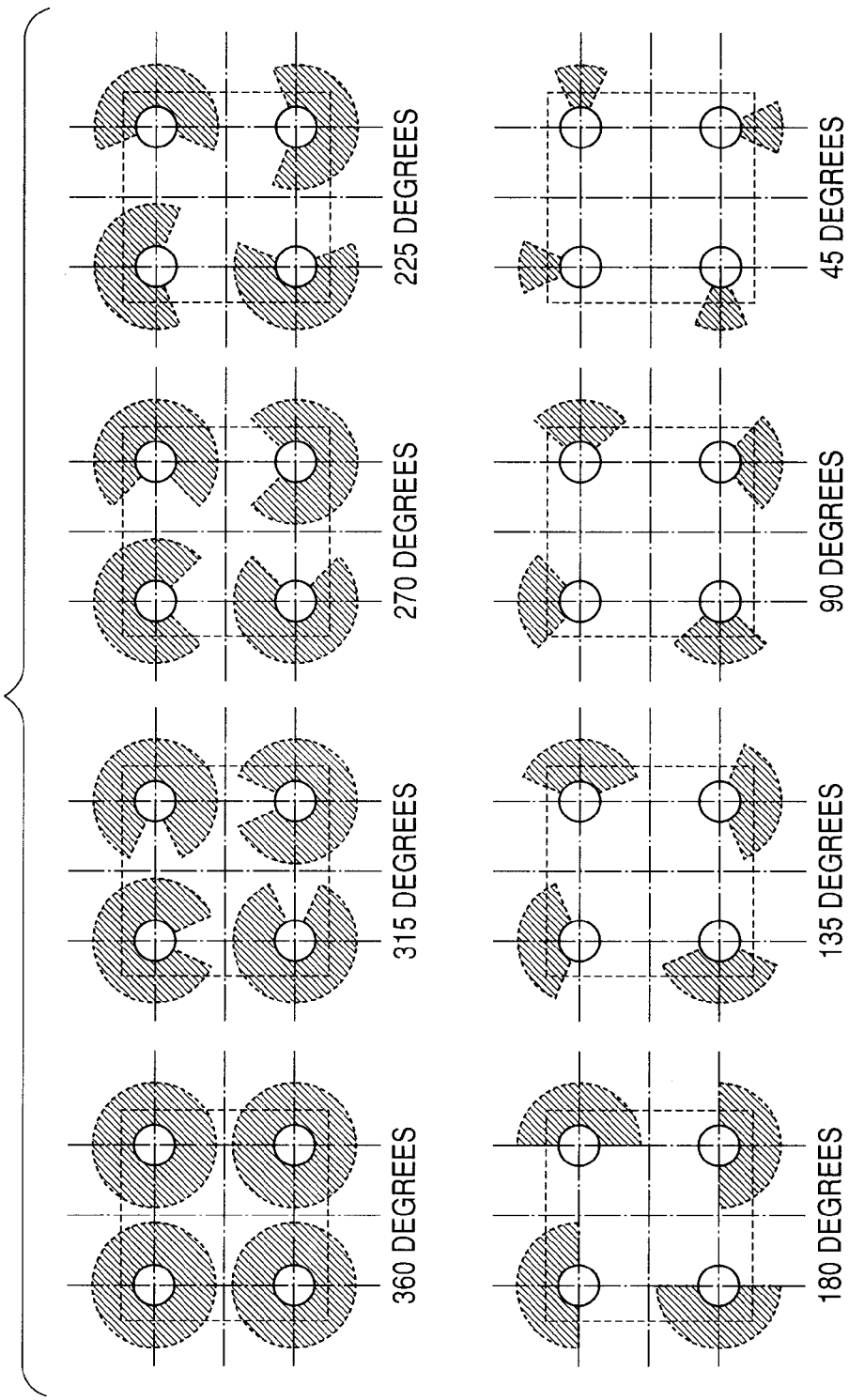

LIQUID DISCHARGE HEAD AND LIQUID DISCHARGE HEAD DEVICE

BACKGROUND OF THE INVENTION

1. Field of the Invention

The present invention relates to a liquid discharge head which discharges liquid droplets as fine liquid droplets, and specifically, to a liquid discharge head suitably used as an inhalation device which is used when a solution including a medicine in a medical field is inhaled into the lungs in the form of mist.

2. Description of the Related Art

Conventionally, a liquid discharge head which discharges a liquid as fine liquid droplets is widely used as an ink jet head in a recording field. Not only is the discharging of liquid droplets but also the controllability of the discharge direction of liquid droplets is required in the ink jet head. In a conventional ink jet head, various proposals for satisfying these requests have been made. For example, Japanese Patent Application Laid-Open No. 2004-001439 discloses an ink jet recording head which discharges liquid droplets from nozzles, which are located at least at ends of a plurality of nozzles arrayed in one direction, in an oblique direction to a discharge surface. The inclining of the nozzles solves the problem that the pitch of joining portions becomes wide, and a gap is formed at a landing position on a sheet when a plurality of these heads is joined together. As methods of discharging liquid droplets obliquely, a formation where there is a height difference in the depth direction of nozzles and a method of performing hydrophilic treatment and water-repellent treatment on the inner wall surfaces of the nozzles asymmetrically have been disclosed. Additionally, Japanese Patent Application Laid-Open No. 2001-105584 discloses a method of arranging at least two energy generating elements at one discharge port to control the driving thereof, thereby changing the discharge directions of liquid droplets at random to solve the concentration unevenness in printing. Discharging ink obliquely in an ink jet recording field in this way has various merits.

However, in a conventional ink jet head in the ink jet recording field, how precise and dense printing dots are filled in high density on a target sheet is the main point of the improvement in the quality of an image. Therefore, energy generating elements are arrayed as densely as possible, one discharge port is arranged for each energy generating element, and discharge ports through which discharge is made according to a driving signal for each energy generating element are made to be as many as possible. This allows compatibility between high resolution and faster printing. Additionally, if the printing dots are dense, resolution improves to a certain degree. However the printing dots may be made dense to such an extent that a person can recognize visually, and it is sufficient if the diameter of discharge ports are reduced to about 10 µm at the utmost.

The aforementioned Japanese Patent Application Laid-Open No. 2004-001439 and Japanese Patent Application Laid-Open No. 2001-105584 have also been devised under the background of the technical fields thereof.

However, in the liquid discharge head used for an inhalation device which is used when a liquid medicine in a medical field is inhaled into the lungs in the form of mist, the discharged droplet diameter is about several micrometers, and optimally, about 2 µm to about 6 µm. Therefore, about 1 to 5 µm is required for the diameter of the discharge ports, and significantly smaller discharge ports are required compared to the discharge ports of the conventional liquid discharge head used in the ink jet recording field. Additionally, in order to shorten inhalation time to relieve burden on a patient, it is necessary to discharge a large amount of liquid droplets in order to prescribe the amount of medicinal solution required in a shortest time possible.

In a case where the amount of discharge per unit time is the same, when the discharged droplet diameter is 3 µm, the same total amount of discharge is not obtained if the number of liquid droplets is not about 40 times the number of liquid droplets compared to the discharged droplet diameter of 10 µm. Due to this, the focal point is how the number of discharged liquid droplets is increased in the liquid discharge head which is used when a liquid medicine in a medical field is inhaled into the lungs in the form of mist compared to the conventional liquid discharge head which is used in the ink jet recording field.

Discharging large amount of liquid droplets in a short time is allowed simply if energy generating elements are increased or discharge ports are increased. However, a discharge head is enlarged, and accordingly, a driving battery also becomes large. Then, as well as the inhalation device becoming enlarged, and the convenience for a patient deteriorating, the cost of an enlarged head becomes high. In order to solve these problems, it is possible to make the interval between discharge ports as narrow as possible to arrange as many discharge ports as possible on an energy generating element as in Japanese Patent Application Laid-Open No. 2003-154655.

However, when the interval between adjacent discharge ports is made to be narrow, a problem has occurred in that discharged liquid droplets come into contact and join up with each other, which produce large liquid droplets, and required optimal liquid droplets cannot be obtained.

In case of the liquid discharge head used for an inhalation device which is used when a liquid medicine in a medical field is inhaled into the lungs in the form of mist, it is necessary to obtain the largest therapeutic effect with as small an amount of a medicinal solution as possible in consideration of physical and economic burdens on the patient. For that purpose, a discharged liquid droplet group needs to include only liquid droplets of an optimal diameter in portions where the liquid droplets are required to reach. This is because, if the diameter of a discharged droplet is greater than the optimal diameter, the droplet may adhere into the inside of the mouth or the bronchus before reaching the lungs, and if the diameter is smaller than the optimal diameter, the droplet may be discharged to the outside of a body during exhalation even when the droplet has reached the lungs.

As mentioned above, in the liquid discharge head used for an inhalation device which is used when a liquid medicine in a medical field is inhaled into the lungs in the form of mist, the diameter of discharge ports is required to be about 1 to 5 µm. These discharge ports are significantly small discharge ports compared to the discharge ports of the conventional liquid discharge head used in the ink jet recording field. Therefore, when a discharge port portion is machined in the shape as described in Japanese Patent Application Laid-Open No. 2004-001439 as the method of inclining the discharge directions in order to prevent liquid droplets discharged from adjacent discharge port from coming into contact and joining up with each other, removal of machining scraps is difficult. When discharge ports are formed not by machining but by photolithography, development scum will remain during exposure and development. Machining of fine holes is difficult by any discharge port operation method. Additionally, in the case of fine holes, the method of dividing the surface property of the inner wall of a discharge port into a hydrophilic property and a water-repellent property by coating is not possible in practice, and is not practical because substantial time and effort are required.

SUMMARY OF THE INVENTION

The object of the invention is to provide a liquid droplet discharge head capable of discharging liquid droplets from adjacent discharge ports without bringing the droplets into contact with each other, in the liquid discharge head in which fine discharge ports are arranged in high density.

Thus, in order to achieve the above object, there is provided a liquid discharge head including an energy generating element which generates energy to be used to discharge a liquid, and a plurality of discharge ports which is formed for each energy generating element and allows the liquid to be discharged therethrough.

The plurality of discharge ports have regions where the angles of contact with the liquid are different around the discharge ports, and the regions in the discharge ports where the contact angles are relatively small are formed at different positions in the plurality of discharge ports, and the liquids discharged from the plurality of discharge ports are discharged in directions away from each other.

As described above, according to the invention, it is possible to solve a problem occurring in a dense arrangement between discharge ports which have a plurality of discharge ports for each energy generating element by making the discharge directions of liquid droplets from adjacent discharge ports different from each other. The problem is that discharged liquid droplets come into contact and join up with each other, which produces large liquid droplets, and required optimal liquid droplets cannot be obtained. Additionally, as the method of making the discharge directions of liquid droplets from the discharge ports different from each other, the angles of contact with a discharge liquid around the discharge ports in the surface of a discharge port plate are made to be a distribution which does not have rotational symmetry. By doing so, even if the diameter of the discharge ports is fine, it is possible to perform the desired operation easily and precisely. Then, a liquid discharge head in which the density of the discharge ports is higher than ever before can be easily manufactured with high precision. As a result, it is possible to provide a compact, convenient, and inexpensive liquid discharge head, and a liquid discharge head device for pulmonary administration having such a liquid discharge head.

Further features of the present invention will become apparent from the following description of exemplary embodiments with reference to the attached drawings.

BRIEF DESCRIPTION OF THE DRAWINGS

FIG. 8 is a view illustrating the positional relationship of hydrophilic portions of four discharge ports arranged on a heater element when the circular arc angle of the hydrophilic portions is changed.

DESCRIPTION OF THE EMBODIMENTS

Figure 1:
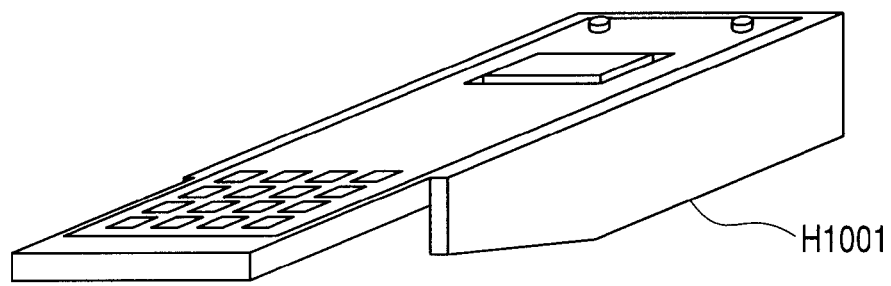
FIG. 1 is an external perspective view of a liquid discharge head of an embodiment of the invention.

Preferred embodiments of the present invention will be described in detail in accordance with the accompanying drawings.

A liquid discharge head of the invention can be suitably used for a device for discharging (also including spraying) fine liquid droplets. Although not particularly limited, the concrete example of the device includes an inhaling device used to administer a solution including medicines in a medical field to a patient's respiratory system. As other applications, the device includes sprays for paint, resist, and a coating agent and steamers.

Here, the liquid discharge head of the invention has one or more energy generating elements which generates discharge energy in a liquid, a space which accommodates the energy generating elements to give energy to the liquid, and a discharge port forming member in which discharge ports are arranged so as to face the energy generating elements. The discharge port forming member is a member (hereinafter referred to as a discharge port plate) which has a flat surface in which a plurality of discharge ports for discharging a liquid as droplets open, and is provided so as to constitute a portion of the wall of the space which accommodates the energy generating elements. The energy generating elements are elements which generate the discharge energy to be given to the liquid, and are accommodated in the space which faces the plurality of discharge ports of the discharge port forming member. Additionally, the discharge port plate has a plurality of discharge ports which discharges the liquid for each energy generating element.

Also, as liquid droplets simultaneously discharged from adjacent discharge ports in the discharge port plate have different discharge directions, the liquid droplets do not come into contact with each other.

In the invention, in order to incline the discharge directions of the liquid droplets with respect to a direction perpendicular to the discharge plane, regions where contact angles with the liquid to be discharged are different are formed around discharge ports. Here, the regions where contact angles are different have a region (hereinafter referred to as a large contact angle region) where the contact angle is relatively large, and a region (hereinafter referred to as a small contact angle region) where the contact angle is relatively small. The small contact angle region is formed around a discharge port of the surface of a discharge plate so as to have distribution which does not have rotational symmetry about the discharge port. The distribution which does not have rotational symmetry means such a distribution that, even if a small contact angle region is rotated about a discharge port, the small contact angle region does not overlap with the pattern of an original small contact angle region until the small contact angle region rotates by 360 degrees.

The regions where contact angles are different are preferably formed so that the difference between the contact angles is 10 degrees or more, and is more preferably formed so that the difference is 30 degrees or more.

The small contact angle region is distributed so that discharge directions of liquid droplets which are adjusted by making contact angles around discharge ports different in this way differ between adjacent discharge ports.

In addition, the discharge directions mean a direction when the discharge plane is seen from the front, are expressed by an angle by which the small contact angle region has rotated from an arbitrary direction about a discharge port as a basis, and may show the relative relationship between discharge directions in a plurality of discharge ports. Additionally, the inclination angle of discharge means the angle of inclination in the discharge directions of liquid droplets from the direction perpendicular to the discharge plane.

When the regions where contact angles are different are formed around discharge ports, liquid droplets are pulled toward a small contact angle region. Therefore, the contact between liquid droplets immediately after discharge between adjacent discharge ports which may contact each other can be prevented by forming small contact angle regions around the respective discharge ports in directions which discharged liquid droplets are separated from each other. The case where contact angles around discharge ports are the same is a case where the discharge directions of discharged liquid droplets deviate from the perpendicular direction, and the direction of the deviation becomes uncertain. Therefore, when the interval between adjacent discharge ports is narrow, there are cases where discharged liquid droplets come into contact with each other. The method of the invention can be used in preventing the possibility of such contact, for example, in a case where discharge ports which have the interval therebetween close to about 10 μm or less are provided, and is more effective because the contact between liquid droplets becomes conspicuous at the interval of about 5 μm or less. Hence, the method can be suitably used in a case where a plurality of discharge ports is arranged for one heater, for example, can be suitably used in cases where the conditions of the following (i) and (ii) can be satisfied. (i) A case where liquid droplets may come into contact with each other when contact angles around discharge ports are the same because the distance between discharge ports which are arranged adjacent to each other in the same energy generating element becomes short. (ii) A case where discharge ports which are adjacent to each other between different energy generating elements are separated from each other by such a distance that liquid droplets do not come into contact with each other. By adjusting discharge directions in a plurality of discharge ports in this way, discharge ports can be arranged in high density as a whole.

By constructing the invention in this way, discharged liquid droplets do not come into contact and join up with each other even in a dense arrangement between discharge ports which have a plurality of discharge ports for each energy generating element. Therefore, liquid droplets which have a target diameter can be obtained. Additionally, in a plurality of discharge ports formed in each of the energy generating elements which are adjacent to each other, discharge ports formed on the side of the adjacent energy generating elements are formed such that the interval between the discharge ports is relatively wide. Therefore, the discharge ports formed on the side of the adjacent energy generating elements do not necessarily perform discharge in directions in which the discharge directions are separated from each other.

Additionally, when the liquid discharge head of the invention is used as a head for the absorption of medicines, it is possible to obtain a construction in which a portion of a device in which the liquid discharge head is arranged is connected to a dispenser of medicines.

The above liquid may be anything in a liquid state, and is not particularly limited. However, for example, solutions including medicines are preferable, and solutions which are specially prescribed so as to be administered to a patient's respiratory system are preferable. In addition, however, the liquid may be suspensions. In addition, the liquid state includes states, such as sol and gel.

Additionally, as the solution or suspension, aqueous liquids can be preferably used because the surface tension thereof is relatively large, and aqueous liquids including mainly water as a solvent are preferably used. Additionally, if compatibility with water is not impaired, hydrophilic solvents such as alcohols such as ethanol, 1-propanol, and isopropyl alcohol, ketones, and carboxylic acid, or solvents such as carboxylic acid ester such as ethyl acetate and hydrocarbon-based compounds such as hexane may also be included. Additionally, for example, when hydrophobic substances or high-molecular solutes are turned into micelle, aqueous liquids including surfactants may be used. Additionally, oily liquids including paint, coating agents, or hydrophobic medicinal substances in an oily solvent may be used.

The above medicines refer to substances which exhibit certain functions and effects on animals, such as the mammals, and are not particularly limited. The above medicine includes, for example, peptides such as insulin, human growth hormone, or gonadotropic hormone, protein preparations such as protein, biopolymers of nucleic acid substances such as oligomer or polynucleotide, medicinal substances such as nicotine, and low-molecular compounds, such as bronchial asthma medicine or anesthetic. These biopolymers and low-molecular compounds are medicines used for lung inhalation, and liquids including these biopolymers and low-molecular compounds, preferably, aqueous liquids can be suitably discharged. Since the surface tension of the liquids is within such a range that the liquids can be generally discharged by an ink jet discharge method, and can also be applied to the discharge of water, for example, liquids with a range of 20 dyn/cm to 73 dyn/cm can be suitably used.

The discharge ports can be formed into a true circle or a substantially round shape, for example, the discharge ports can have an aperture of 2 μm to 6 μm, preferably, 1 μm to 5 μm. The discharge velocity of liquid droplets can be set to, for example, 5 m/s to 20 m/s. The mean particle diameter of liquid droplets to be discharged can be set to 1 μm to 5 μm.

A method of forming regions where at least one of the surface free energy (surface tension) and surface roughness is different, in regions around discharge ports in the surface of a discharge plate can be used as a method of forming the regions where contact angles are different. Hereinafter, a case where the region where the contact angle is relatively small has a region (hereinafter referred to as a hydrophilic portion) which has a hydrophilic property, and the region where the contact angle is large has a region (hereinafter referred to as a water-repellent portion) which has a water-repellent property will be described as an example. In addition, as long as the regions where contact angles are different can be formed, both the different regions may be hydrophilic surfaces and the contact angles may be different depending on differences in the hydrophilic property, or both the different regions may be water-repellent surfaces and the contact angles may be different depending on differences in a water-repellent property.

The regions where contact angles are different can be formed in the following order, for example. First, surfaces which have a water-repellent property are formed around discharge ports of a discharge plate. This may be performed by using a discharge plate made of a water-repellent material, such as a fluorine-based material or by forming a water-repellent layer on the surface of a discharge plate. Next, hydrophilic portions are formed in predetermined regions around discharge ports. The hydrophilic portions are formed by being subjected to hydrophilic treatment by well-known methods, such as excimer laser irradiation and corona discharge. Solutions including substances which promote hydrophilization, such as boric acid, may be added to regions to be subjected to hydrophilic treatment.

Additionally, the regions where contact angles are different can be formed around discharge ports of a discharge plate by a method of changing surface roughness, and well-known methods can be used as a method of adding surface roughness. For example, the contact angles can be relatively made to be large by performing roughening treatment on a discharge plate which has a water-repellent property so that the value (Ra) of the surface roughness becomes about 0.1 to 1.6, thereby making water-repellent property of the roughened portion higher than other portions. This enables the discharge directions of liquid droplets to be turned toward a non-roughened region where the contact angle becomes relatively small. Additionally, for example, even if roughness is slightly added in the discharge plate which has a hydrophilic property, the hydrophilic property of the roughened region can be made higher than that of other portions, and the discharge of liquid droplets can be inclined toward the region to which roughness is added.

As the hydrophilic portions, those having a circular-arc shape or a shape having symmetry may be used from the viewpoint that adjustment is made in order to control discharge directions. Additionally, the hydrophilic portions have a portion (start end) which is in contact with a discharge port in the surface of a discharge plate, and an outward extending portion (a terminal end). The outward extending portion may be provided so as to include the whole range where liquid droplets come into contact with each other, and may be set so as to include a portion of the range where liquid droplets come into contact with each other as long as discharge directions are controlled.

In such distribution of the hydrophilic portions, when the shapes of hydrophilic portions of respective discharge ports are different, the distribution of the hydrophilic portions and the discharge directions are also different. Therefore, a distribution arrangement can be determined in consideration of the relationship between the shapes of the hydrophilic portions of the respective discharge ports, and the discharge directions. From the viewpoint of control of the discharge directions of the respective discharge ports, the respective discharge ports have hydrophilic portions of the same shape, and the relative positions around the respective discharge ports are made different, so that the control can be made.

First, the construction of the liquid discharge head device will be described with reference to FIGS. 1 to 4. FIGS. 1 to 4 are an explanatory view for describing a liquid discharge head device using heater elements which is suitable for implementation of the invention.

A conventional liquid discharge head H1001 of FIG. 1 can be utilized as an inhaling device. The liquid discharge head device H1001 is a side shooter type liquid discharge head of the method which performs discharge using a heating element which generates the heat energy for causing film boiling in a liquid according to an electric signal. In addition, although the construction using the heater elements has been described in the above description, the energy generating elements are not particularly limited to the heater elements, and vibrational-energy generating elements like piezoelectric elements can be used.

Figure 2:
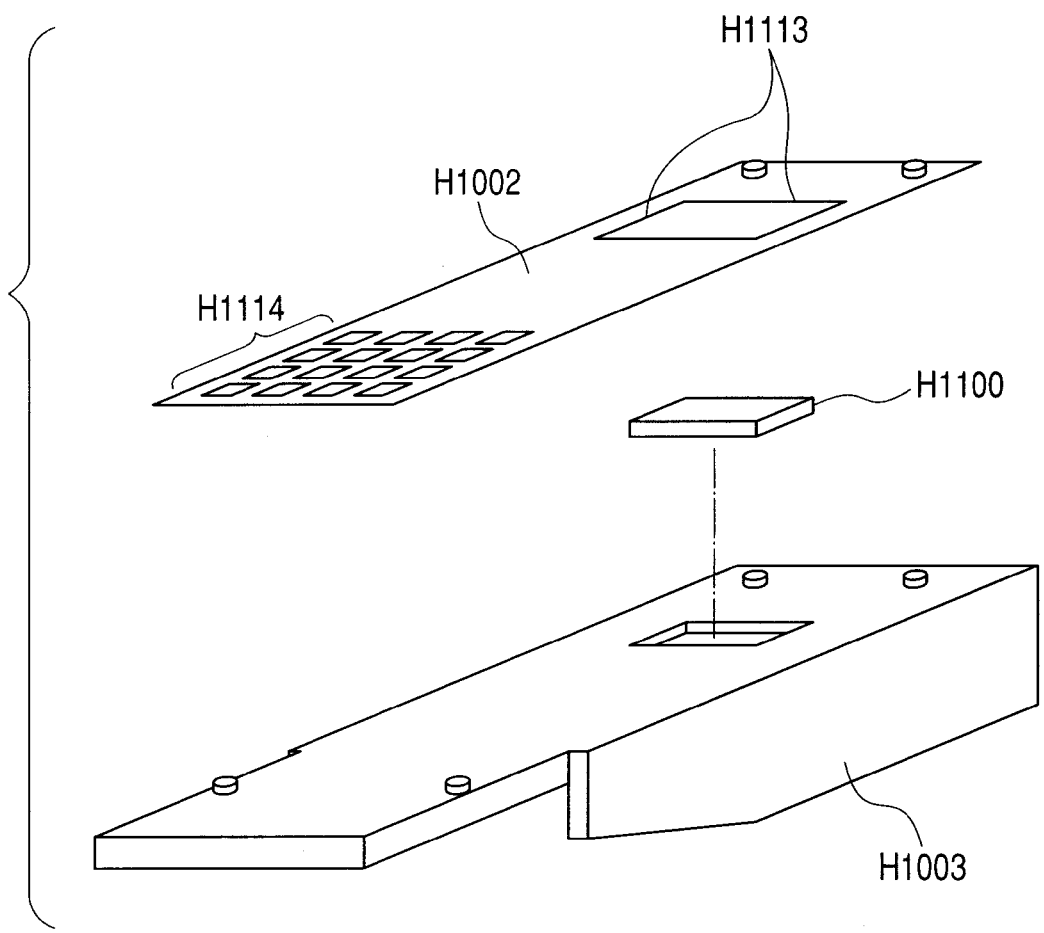
FIG. 2 is an exploded perspective view of the liquid discharge head illustrated in FIG. 1.

Next, respective components which constitute the liquid discharge head device H1001 will be described step by step. FIG. 2 is an exploded perspective view of the liquid discharge head device H1001 of FIG. 1. The liquid head device H1001, as illustrated in the exploded perspective view of FIG. 2, includes a heater element substrate H1100, an electric wiring tape H1002, and a tank holder H1003. The electric wiring tape H1002 has a space H1113 in which the heater element substrate is arranged, and an electrical connection H1114. Next, the tank holder H1003 is formed by resin molding, for example. The tank holder H1003 had a connection port for guiding a liquid to a liquid supply port H1102 (refer to FIG. 3) of the heater element substrate H1100 from a liquid tank (not illustrated), and also has partially a function of holding the liquid tank (not illustrated) which can be detached and attached. For example, solutions including medicines are put into and stored in this liquid tank.

Figure 3:
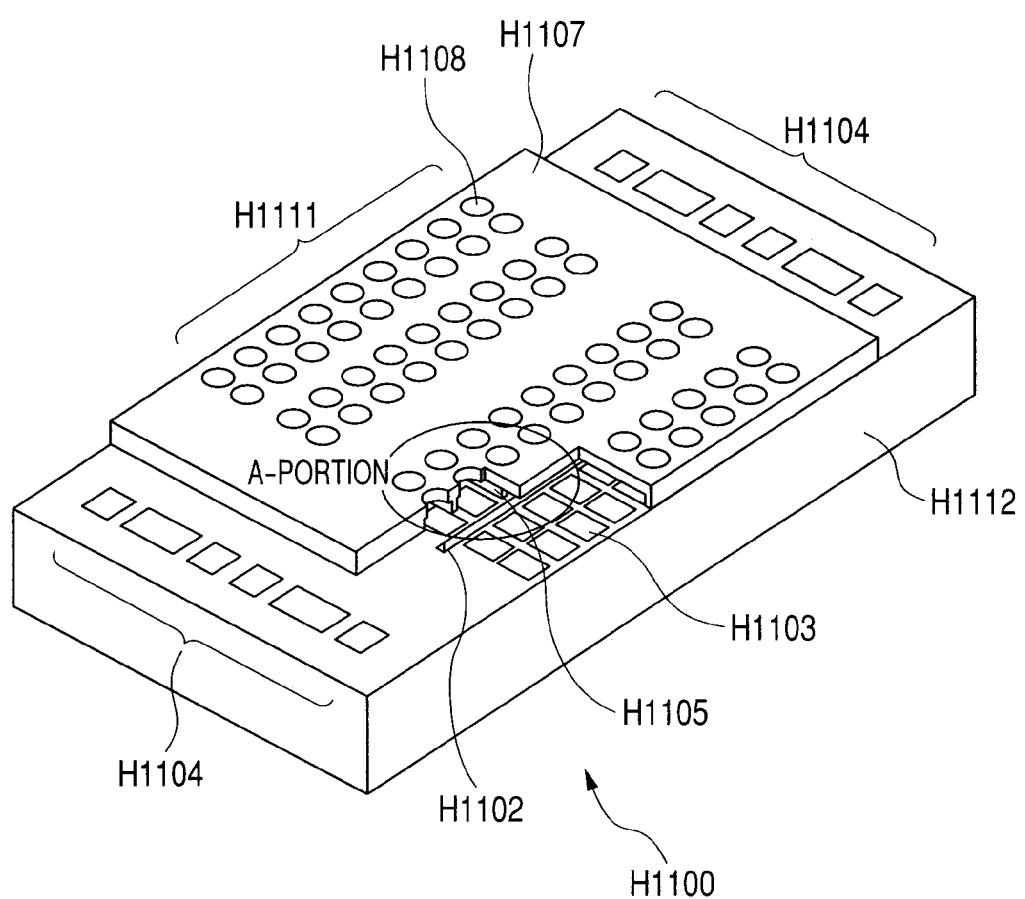
FIG. 3 is a perspective view illustrating that a heater element substrate illustrated in FIG. 2 is partially broken off.
Figure 4:
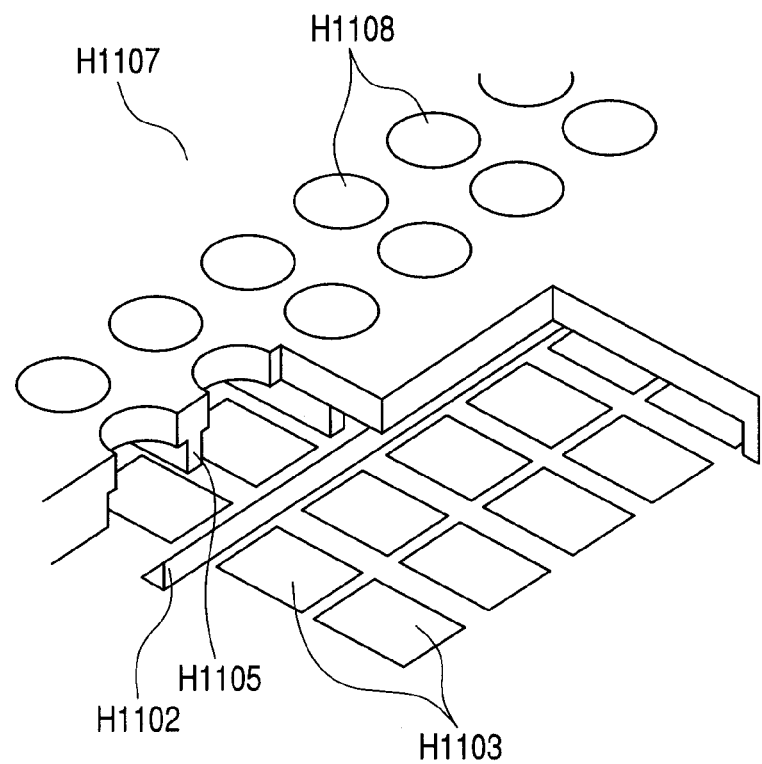
FIG. 4 is a detail view of an A-portion of FIG. 3.

FIG. 3 is a perspective view illustrating an exploded portion in order to describe the construction of the heater element substrate H1100. In the heater element substrate H1100, for example, the liquid supply port H1102 which has a long groove-shaped through port as a liquid flow passage is formed in an Si substrate H1112 with a thickness of 0.5 to 1 mm by methods such as anisotropic etching and sandblasting utilizing the crystal orientation of Si. Additionally, two rows of heater elements H1103 are respectively arrayed on both sides of the liquid supply port H1102, and electric wiring and a passivation film (not illustrated) which supply electric power to the heater elements H1103 are formed by a film forming technique. Moreover, electrode portions H1104 for supplying electric power to the electric wiring are arrayed on both outer sides of the heater element substrate H1100. A flow passage wall H1105 is formed on the Si substrate H1112 so as to have a liquid flow passage H1106 communicating with the liquid supply port H1102 and surround two pairs of heater elements, thereby constituting a liquid chamber. The flow passage wall H1105 is made by photolithography, using a photosensitive resin material. A discharge port plate H1107 provided with discharge ports is joined to an upper portion of the flow passage wall with a polyimide sheet. As a result, the space for giving energy to a discharge liquid is formed. The discharge ports H1108 are formed by an excimer laser while recognizing heater element positions through a polyimide sheet. The plurality of discharge ports forms a discharge port group H1111 in the discharge port plate H1107. FIG. 4 illustrates an A-portion illustrated in FIG. 3 in an enlarged manner. Water-repellent treatment is performed on the surface of the discharge port plate H1107. The method of water-repellent treatment is performed by applying a water-repellent material CTX-CZ 5A (Asahi Glass Co., Ltd.) while nitrogen gas is gently jetted from discharge ports so that water-repellent material does not enter the discharge ports. The heater element substrate H1100 and the electric wiring tape H1002 are assembled to the tank holder H1003, thereby completing a liquid discharge head. The liquid supplied from the liquid supply port H1102 is discharged from the discharge ports H1108 which are provided to face the heater elements H1103 by the bubbles generated by the heater elements H1103.

A driving signal to the heater elements H1103 makes 128 adjacent heater elements (64 pairs of heater elements in which every two heater elements are arranged in one liquid chamber) collectively driven as a set. Since the liquid discharge head has a number of heater elements, a discharge liquid is discharged from the liquid discharge head by setting 128 heater elements as one driven group to make the heater elements sequentially driven.

Hereinafter, the method of forming regions where contact angles are different around a plurality of discharge ports in the liquid discharge head of the invention, and the way that regions are distributed whereby contact angles between adjacent discharge ports are different will be described while describing some embodiments.

Embodiment 1

Figure 5:
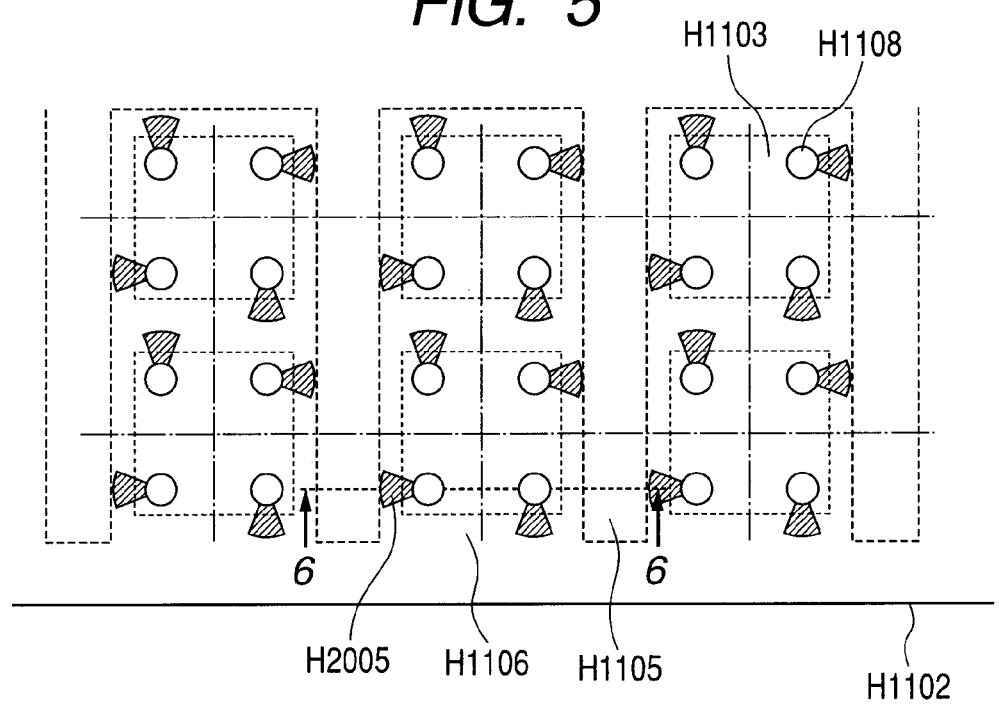
FIG. 5 is a plan view illustrating some of discharge ports illustrated in FIG. 3.
Figure 6:
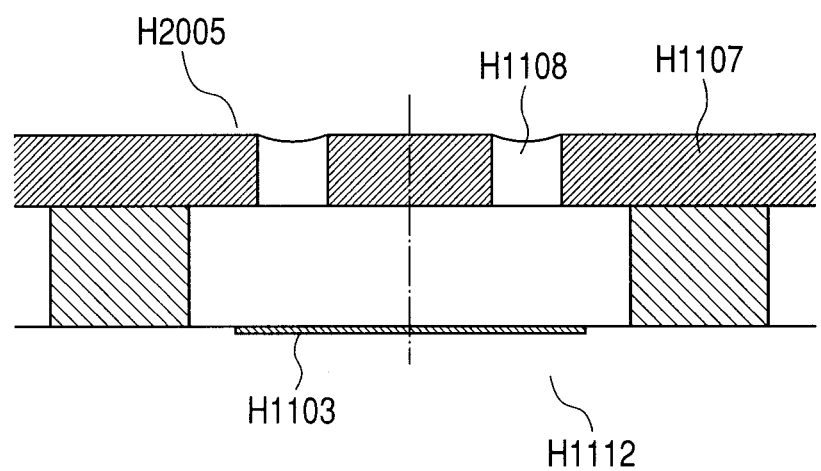
FIG. 6 is a sectional view taken along a line 6-6 of FIG. 5.
Figure 7:
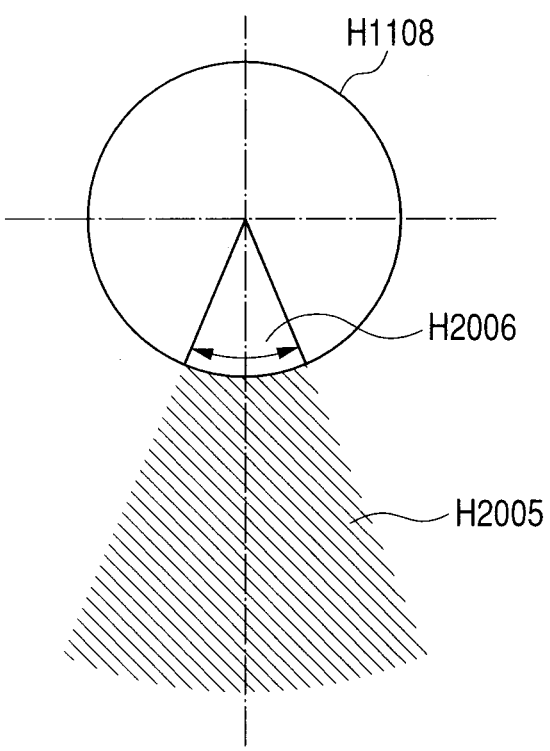
FIG. 7 is an enlarged plan view of a discharge port H1108 of FIGS. 5 and 6.

FIGS. 5 to 7 illustrate one embodiment of the liquid discharge head of the invention which has regions where contact angles are different around discharge ports. FIG. 5 is a plan projection view of the liquid discharge head seen from the direction perpendicular to the substrate of the liquid discharge head, FIG. 6 is a sectional view taken along a line 6-6 in FIG. 5, and FIG. 7 is an enlarged view of a discharge port in FIG. 5.

In the liquid discharge head of the form illustrated in FIG. 5 to FIG. 7, the heater elements H1103 that are energy generating elements for discharging liquid were provided on the Si substrate H1112. The heater elements H1103 had a square shape which is 15 μm long and 15 μm wide, and a plurality of heater element rows each including two heater elements H1103 was arranged at pitches of 25 μm along the liquid supply port H1102. The two heater element rows were arranged at intervals of 20 μm. The flow passage wall H1105 was formed so as to have a liquid flow passage H1106 with a width of 19 μm communicating with the liquid supply port H1102 and surround two pairs of heater elements. The flow passage wall was formed by photolithography, using a photosensitive resin material. The height of the flow passage wall was set to 5 μm, and the thickness of the flow passage wall which separates two pairs of adjacent heater element rows was set to a width of 6 μm. Although FIG. 5 illustrates only a total of six heater elements in which two heater elements H1103 are provided in each of three liquid flow passages H1106, practically, a plurality of heater elements H1103 are arrayed on one Si substrate H1112. In addition, the energy generating elements are not limited to heater elements like the heaters, and may be vibrational-energy generating elements like piezoelectric elements. Additionally, instead of the Si substrate H1112, the substrate can also be formed from, for example, glass, ceramic, resin, and metals other than Si.

Next, the space was formed for joining a polyimide sheet with a thickness of 5 μm which becomes a discharge port plate and giving energy to a discharge liquid.

Next, the discharge ports H1108 were formed in the discharge port plate at the upper position of the heater elements by an excimer laser, while heater element positions are observed through the polyimide sheet. Four discharge ports with a diameter of 3 μm were made at positions with the equal distance from the center of a heater element at pitches of 10 μm in every heater element. In addition, the distance between discharge ports which are adjacent to each other between two rows of heater elements in the same liquid flow passage was 12.2 μm, and the distance between discharge ports which are adjacent to each other between two heater elements in different liquid flow passages was 12.2 μm. Next, a sub-product called debris generated by ablation was removed. Next, the surface of the discharge port plate was subjected to water-repellent treatment by applying a water-repellent material CTX-CZ 5A (Asahi Glass Co., Ltd.) while nitrogen gas is gently jetted from discharge ports so that water-repellent material does not enter the discharge ports.

Next, a 3% boric acid aqueous solution serving as a hydrophilization promoting substance was dropped on a water-repellent layer of the surface of the discharge port plate H1107, and a quartz glass mask was superimposed in alignment with the discharge port positions. The quartz glass mask was used after portions other than portions corresponding to the hydrophilic portions were subjected to light-shielding treatment. Next, a dielectric barrier discharge excimer lamp ER200-172 (made by Ushio, Inc.) whose emission center wavelength is 172 nm irradiated the quartz glass mask for 5 minutes from right above the quartz glass mask, and thereby the hydrophilic portions H2005 were formed.

The method of forming water-repellent portions and hydrophilic portions, in addition to the present method, can also be performed by a method of changing fine surface roughness of a surface, a method of treating the surface of a water-repellent material by corona discharge to perform hydrophilization of the surface, a method of removing a water-repellent layer locally using a laser, or combined methods thereof.

In this instance, hydrophilic portions with a desired shape were formed around discharge ports, with the discharge port plate as a water-repellent surface. Contrary to this, the distribution of contact angles around discharge ports can also be changed by forming water-repellent portions with a desired shape around discharge ports, with the discharge port plate as a hydrophilic surface.

The positional relationship between a discharge port and a hydrophilic portion will be described referring to FIG. 7. A circular-arc hydrophilic portion H2005 with a radius of 4.5 μm which has the same center as the discharge port H1108 was formed on the peripheral surface of the discharge port. FIG. 7 illustrates a case where an angle H2006 of a circular arc is 45 degrees. Four discharge ports were formed in every heater element as illustrated in FIG. 5 by changing the positions of hydrophilic portions around the discharge ports by every 90 degrees.

Additionally, seven types of liquid discharge heads were made in which the angles H2006 of circular arcs of hydrophilic portions are 45 degrees, 90 degrees, 135 degrees, 180 degrees, 225 degrees, 270 degrees, and 315 degrees. Additionally, as comparative examples, a liquid discharge head was prepared in which the angles H2006 of circular arcs of hydrophilic portions around discharge ports are 360 degrees, and a liquid discharge head was prepared in which hydrophilic treatment is not performed and the periphery of a discharge port remains in a water-repellent state. FIG. 8 illustrates an arrangement shape in which four discharge ports are formed in one heater element, and hydrophilic portions H2005 were formed at every circular arc angle H2006.

The advance contact angles of the water-repellent portions and the hydrophilic portions were measured using a monitor unit for measurement of contact angles. The contact angle of water whose surface tension is 73 dyne/cm was 90 degrees in the water-repellent portions and 55 degrees in the hydrophilic portions. Additionally, discharge evaluation tests of seven types of liquid discharge heads in which the angles H2006 of the circular arcs of the hydrophilic portions are 45 degrees, 90 degrees, 135 degrees, 180 degrees, 225 degrees, 270 degrees, and 315 degrees were performed with water whose surface tension is dyne/cm as discharge liquid. Additionally, the discharge state of liquid droplets was observed using a discharged liquid droplet magnification observation system. Additionally, a particle-size-distribution profile based on mean particle diameter and volume were measured using a laser diffraction particle-size-distribution measuring instrument made by Malvern Instruments, Ltd.

Discharge evaluation tests were similarly performed on the liquid discharge head of the comparative example in which the angles of circular arcs are 360 degrees, and the liquid discharge head of the comparative example in which hydrophilic treatment is not performed and the peripheries of discharge ports remain in a water-repellent state, and the discharge state of liquid droplets was observed using a discharged liquid droplet magnification observation system. Additionally, a particle-size-distribution profile based on mean particle diameter and volume were measured using a laser diffraction particle-size-distribution measuring instrument made by Malvern Instruments, Ltd.

As a result, the mean particle diameter of all the liquid droplets, which were discharged in seven types of liquid discharge heads in which hydrophilic portions where the angles H2006 of circular arcs of the hydrophilic portions are 45 degrees, 90 degrees, 135 degrees, 180 degrees, 225 degrees, 270 degrees, and 315 degrees were formed around discharge ports, was about 3.8 to 4.5 μm. The half-value width of a relative particle weight curve based on volume which shows the broad degree of particle size distribution was about 1.0. Although the discharge state of a number of liquid droplets was observed by selecting discharge ports of the heads at random, the discharge state was stable with no sign that discharged liquid droplets had come into contact and joined up with each other. Additionally, when the discharge directions of liquid droplets were observed from front positions which face discharge ports, a state was observed where a liquid droplet is discharged while being inclined so as to be pulled in the direction of a central portion of a hydrophilic portion around a discharge port.

The mean particle diameter of all the liquid droplets, which were discharged in the liquid discharge head of the comparative example in which the angles of circular arcs of hydrophilic portions around discharge ports are 360 degrees, and the liquid discharge head of the comparative example in which hydrophilic treatment is not performed and the peripheries of discharge ports remain in a water-repellent state, was about 5.5 to 6.5 μm. The half-value width of a relative particle weight curve based on volume which shows the broad degree of particle size distribution was about 1.6. When the discharge state of a number of liquid droplets was observed by selecting discharge ports of the heads at random, a plurality of spots were observed where liquid droplets discharged from adjacent discharge ports had come into contact and joined up with each other.

Due to this, the followings were confirmed as a result of having performed discharge evaluation using water whose surface tension is 73 dyne/cm. That is, it was confirmed that coming into contact and joining up of liquid droplets discharged from adjacent discharge ports did not occur by making the distribution of hydrophilic portions (small contact angle regions) around discharge ports into the distribution which does not have rotational symmetry about the discharge ports, and adjusting the positions of the hydrophilic portions so that the discharge directions of the adjacent discharge ports are different. Additionally, it was confirmed that particle diameter which is sufficiently good and uniform compared to the comparative examples are obtained even in terms of the particle size distribution.

Embodiment 2

Similarly to Embodiment 1, seven types of liquid discharge heads were made in which the angles H2006 of circular arcs of the hydrophilic portions are 45 degrees, degrees, 135 degrees, 180 degrees, 225 degrees, 270 degrees, and 315 degrees. As comparative examples, similarly to Embodiment 1, a liquid discharge head was prepared in which the angles H2006 of circular arcs are 360 degrees, and a liquid discharge head was prepared in which hydrophilic treatment is not performed and the peripheries of discharge ports remain in a water-repellent state.

The advance contact angles of the water-repellent portions and the hydrophilic portions were measured using a monitor unit for measurement of contact angles. The contact angle of ink whose surface tension is 25 dyne/cm was 70 degrees in the water-repellent portions and 45 degrees in the hydrophilic portions.

Except that ink whose surface tension is 25 dyne/cm was used as a discharge liquid, the discharge evaluation tests of the liquid discharge heads were performed similarly to Embodiment 1.

As a result, the mean particle diameter of all the liquid droplets, which were discharged in seven types of liquid discharge heads in which hydrophilic portions in which the angles H2006 of circular arcs of the hydrophilic portions are 45 degrees, 90 degrees, 135 degrees, 180 degrees, 225 degrees, 270 degrees, and 315 degrees were formed around discharge ports, was about 3.2 to 4.2 μm. The half-value width of a relative particle weight curve based on volume which shows the broad degree of particle size distribution was about 1.2. Although the discharge state of a number of liquid droplets was observed by selecting discharge ports of the heads at random, the discharge state was stable with no sign that discharged liquid droplets had come into contact and joined up with each other. Additionally, when the discharge directions of liquid droplets were observed from front positions of discharge ports, a state was observed where a liquid droplet is discharged while being inclined so as to be pulled in the direction of a central portion of a hydrophilic portion around a discharge port.

The mean particle diameter of all the liquid droplets, which were discharged in the liquid discharge head of the comparative example in which the angles of circular arcs of hydrophilic portions are 360 degrees, and the liquid discharge head of the comparative example in which hydrophilic treatment is not performed and the peripheries of discharge ports remain in a water-repellent state, was about 5.0 to 6.5 μm. The half-value width of a relative particle weight curve based on volume which shows the broad degree of particle size distribution was about 1.7. When the discharge state of a number of liquid droplets was observed by selecting discharge ports of the heads at random, a plurality of spots were observed where liquid droplets discharged from adjacent discharge ports has come into contact and joined up with each other.

Due to this, the followings were confirmed as a result of having performed discharge evaluation using ink whose surface tension is 25 dyne/cm. That is, it was confirmed that contacting and joining of liquid droplets discharged from adjacent discharge ports did not occur by making the distribution of hydrophilic portions (small contact angle regions) around discharge ports into the distribution which does not have rotational symmetry about the discharge ports, and adjusting the positions of the hydrophilic portions so that the discharge directions of the adjacent discharge ports are different. Additionally, it was confirmed that particle diameter which is sufficiently good and uniform compared to the comparative examples are obtained even in terms of the particle size distribution.

Embodiment 3

Except for the treatment time when hydrophilic portions are formed, four liquid discharge heads in which the angles of circular arcs of hydrophilic portions around discharge ports are 45 degrees were manufactured similarly to Embodiment 1. The four liquid discharge heads were treated while changing hydrophilization treatment time to 4 minutes, 3 minutes, 2 minutes, and 1 minute. The advance contact angles of the water-repellent portions and the hydrophilic portions were measured using a monitor unit for measurement of contact angles. The contact angle of water whose surface tension is 73 dyne/cm was 90 degrees in the water-repellent portions. In the hydrophilic portions, the contact angles were 65 degrees, 75 degrees, 80 degrees, and 85 degrees for the hydrophilization treatment times of 4 minutes, 3 minutes, 2 minutes, and 1 minute.

As comparative examples, similarly to Embodiment 1, a liquid discharge head was prepared in which the angles H2006 of circular arcs of hydrophilic portions are 360 degrees and the hydrophilization treatment time of the hydrophilic portions is 4 minutes, and a liquid discharge head was prepared in which hydrophilic treatment is not performed and the peripheries of discharge ports remain in a water-repellent state.

Using water whose surface tension is 73 dyne/cm as a discharge liquid, the discharge evaluation tests of the liquid discharge heads were performed similarly to Embodiment 1.

As a result, the mean particle diameter of all the liquid droplets, which were discharged in liquid discharge heads in which the contact angles of hydrophilic portions around discharge ports are 65 degrees, 75 degrees, and 80 degrees, was about 3.8 to 4.5 μm. The half-value width of a relative particle weight curve based on volume which shows the broad degree of particle size distribution was about 1.0. Although the discharge state of a number of liquid droplets was observed by selecting discharge ports of the heads at random, the discharge state was stable with no sign that discharged liquid droplets had come into contact and joined up with each other. Additionally, when the discharge directions of liquid droplets were observed from front positions which face discharge ports, a state was observed where a liquid droplet is discharged while being inclined so as to be pulled in the direction of a central portion of a hydrophilic portion around a discharge port.

The mean particle diameter of the liquid droplets discharged in the following three discharge heads was about 5.5 to 6.5 μm. A liquid discharge head in which the contact angles of hydrophilic portions around discharge ports are 85 degrees, a liquid discharge head of a comparative example in which the angles of circular arcs of hydrophilic portions are 360 degrees, and a liquid discharge head of a comparative example in which hydrophilic treatment is not performed and the peripheries of discharge ports remains in a water-repellent state. The half-value width of a relative particle weight curve based on volume which shows the broad degree of particle size distribution was about 1.6.

When the discharge state of a number of liquid droplets was observed by selecting discharge ports of the heads at random, a plurality of spots were observed where liquid droplets discharged from adjacent discharge ports had come into contact and joined up with each other.

Due to this, the following was confirmed as a result of having performed discharge evaluation using water whose surface tension is 73 dyne/cm. That is, it was confirmed that coming into contact and joining of liquid droplets discharged from adjacent discharge ports did not occur when the difference between the contact angles of the water-repellent portions and the hydrophilic portions was 10 degrees or more, in the case of the distribution where the hydrophilic portions (small contact angle regions) around the discharge ports do not have rotational symmetry about the discharge ports.

Embodiment 4

Four liquid discharge heads in which the angles of circular arcs of hydrophilic portions around discharge ports are 45 degrees were manufactured similarly to Embodiment 3. The four liquid discharge heads were treated while changing hydrophilization treatment time to 4 minutes, 3 minutes, 2 minutes, and 1 minute.

Since the ink whose surface tension is 25 dyne/cm is used as a discharge liquid, the contact angles of the ink were measured similarly to Embodiment 3. The contact angle was 70 degrees in the water-repellent portions. In the hydrophilic portions, the contact angles were 45 degrees, 55 degrees, 60 degrees, and 65 degrees for the hydrophilization treatment times of 4 minutes, 3 minutes, 2 minutes, and 1 minute.

As comparative examples, similarly to Embodiment 3, a liquid discharge head was prepared in which the angles H2006 of circular arcs of hydrophilic portions are 360 degrees and the treatment time of the hydrophilic portions is 4 minutes, and a liquid discharge head was prepared in which hydrophilic treatment is not performed and the peripheries of discharge ports remain in a water-repellent state.

The discharge evaluation tests of the liquid discharge heads were performed similarly to Embodiment 3. As a result, the mean particle diameter of all the liquid droplets, which were discharged in liquid discharge heads in which the contact angles of hydrophilic portions around discharge ports are 45 degrees, 55 degrees, and 60 degrees, was about 3.2 to 4.2 μm. The half-value width of a relative particle weight curve based on volume which shows the broad degree of particle size distribution was about 1.2. Although the discharge state of a number of liquid droplets was observed by selecting discharge ports of the heads at random, the discharge state was stable with no sign that discharged liquid droplets had come into contact and joined up with each other. Additionally, when the discharge directions of liquid droplets were observed from front positions which face discharge ports, a state was observed where a liquid droplet is discharged while being inclined so as to be pulled in the direction of a central portion of a hydrophilic portion around a discharge port.

The mean particle diameter of the liquid droplets discharged in the following three discharge heads was about 5.0 to 6.5 μm. A liquid discharge head in which the contact angles of hydrophilic portions around discharge ports are 65 degrees, a liquid discharge head of a comparative example in which the angles of circular arcs of hydrophilic portions are 360 degrees, and a liquid discharge head of a comparative example in which hydrophilic treatment is not performed and the peripheries of discharge ports remains in a water-repellent state. The half-value width of a relative particle weight curve based on volume which shows the broad degree of particle size distribution was about 1.7.

When the discharge state of a number of liquid droplets was observed by selecting discharge ports of the heads at random, a plurality of spots where liquid droplets discharged from adjacent discharge ports had come into contact and joined up with each other were observed.

Due to this, the following was confirmed as a result of having performed discharge evaluation using ink whose surface tension is 25 dyn/cm. That is, it was confirmed that coming into contact and joining of liquid droplets discharged from adjacent discharge ports did not occur when the difference between the contact angles of the water-repellent portions and the hydrophilic portions was 10 degrees or more, in the case of the distribution where the angles of contact with the discharge liquid around the discharge ports do not have rotational symmetry.

The results of Embodiments 1 to 4 described above are put together and illustrated in Table 1.

TABLE 1

| Embodiment | Discharge Liquid (Surface Tension) | Hydrophilic Treatment Time (min) | Angle of Circular Arc of Hydrophilic Portion (Degrees) | Contact Angle of Water-Repellent Portion (Degrees) | Contact Angle of Hydrophilic Portion (Degrees) | Mean Particle Diameter of Liquid Droplet (μm) | Half-Value Width | Contact of Liquid Droplet |
|---|---|---|---|---|---|---|---|---|
| 1 | Water (73 dyn/cm) | 5 | 45 | 90 | 55 | 3.8-4.5 | 1.0 | No |
| 1 | Water (73 dyn/cm) | 5 | 90 | 90 | 55 | 3.8-4.5 | 1.0 | No |
| 1 | Water (73 dyn/cm) | 5 | 135 | 90 | 55 | 3.8-4.5 | 1.0 | No |
| 1 | Water (73 dyn/cm) | 5 | 180 | 90 | 55 | 3.8-4.5 | 1.0 | No |
| 1 | Water (73 dyn/cm) | 5 | 225 | 90 | 55 | 3.8-4.5 | 1.0 | No |
| 1 | Water (73 dyn/cm) | 5 | 270 | 90 | 55 | 3.8-4.5 | 1.0 | No |
| 1 | Water (73 dyn/cm) | 5 | 315 | 90 | 55 | 3.8-4.5 | 1.0 | No |
| 1 | Water (73 dyn/cm) | 5 | 360 | 90 | 55 | 5.5-6.5 | 1.6 | Yes |
| 1 | Water (73 dyn/cm) | 5 | None | 90 | — | 5.5-6.5 | 1.6 | Yes |
| 2 | Ink (25 dyn/cm) | 5 | 45 | 70 | 45 | 3.2-4.2 | 1.2 | No |
| 2 | Ink (25 dyn/cm) | 5 | 90 | 70 | 45 | 3.2-4.2 | 1.2 | No |
| 2 | Ink (25 dyn/cm) | 5 | 135 | 70 | 45 | 3.2-4.2 | 1.2 | No |
| 2 | Ink (25 dyn/cm) | 5 | 180 | 70 | 45 | 3.2-4.2 | 1.2 | No |
| 2 | Ink (25 dyn/cm) | 5 | 225 | 70 | 45 | 3.2-4.2 | 1.2 | No |
| 2 | Ink (25 dyn/cm) | 5 | 270 | 70 | 45 | 3.2-4.2 | 1.2 | No |
| 2 | Ink (25 dyn/cm) | 5 | 315 | 70 | 45 | 3.2-4.2 | 1.2 | No |
| 2 | Ink (25 dyn/cm) | 5 | 360 | 70 | 45 | 5.0-6.5 | 1.7 | Yes |
| 3 | Water (73 dyn/cm) | 4 | 45 | 90 | 65 | 3.8-4.5 | 1.0 | No |
| 3 | Water (73 dyn/cm) | 3 | 45 | 90 | 75 | 3.8-4.5 | 1.0 | No |
| 3 | Water (73 dyn/cm) | 2 | 45 | 90 | 80 | 3.8-4.5 | 1.0 | No |
| 3 | Water (73 dyn/cm) | 1 | 45 | 90 | 85 | 5.5-6.5 | 1.6 | Yes |
| 3 | Water (73 dyn/cm) | 4 | 360 | 90 | 65 | 5.5-6.5 | 1.6 | Yes |
| 3 | Water (73 dyn/cm) | None | None | 90 | — | 5.5-6.5 | 1.6 | Yes |
| 4 | Ink (25 dyn/cm) | 4 | 45 | 70 | 45 | 3.2-4.2 | 1.2 | No |
| 4 | Ink (25 dyn/cm) | 3 | 45 | 70 | 55 | 3.2-4.2 | 1.2 | No |
| 4 | Ink (25 dyn/cm) | 2 | 45 | 70 | 60 | 3.2-4.2 | 1.2 | No |
| 4 | Ink (25 dyn/cm) | 1 | 45 | 70 | 65 | 5.0-6.5 | 1.7 | Yes |
| 4 | Ink (25 dyn/cm) | 4 | 360 | 70 | 45 | 5.0-6.5 | 1.7 | Yes |
| 4 | Ink (25 dyn/cm) | None | None | 70 | — | 5.0-6.5 | 1.7 | Yes |

Hydrophilic Treatment: 3% Boric Acid Aqueous Solution + Excimer Lamp Irradiation Treatment While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-106254, filed on Apr. 24, 2009, which is hereby incorporated by reference herein in its entirety.

What is claimed is:

1. A liquid discharge head comprising:
a substrate on which an energy generating element which generates energy to be used to discharge a liquid is formed; and
a plurality of discharge ports having circle shape and which is formed for each energy generating element to allow the liquid to be discharged therethrough in a direction intersecting with the substrate, the plurality of discharge ports being formed at a position facing the energy generating element,
wherein the plurality of discharge ports have regions where the angles of contact with the liquid are different, around the discharge ports, and
wherein in the regions in the discharge ports where the contact angles are relatively small at different positions in the plurality of discharge ports, and the liquids discharged from the plurality of discharge ports are discharged in directions away from each other.

2. The liquid discharge head according to claim 1, wherein the regions where the contact angles are different from each other are formed by making at least one of surface free energy and surface roughness different in regions around the discharge ports in the surface of a discharge plate to be formed with the plurality of discharge ports.

3. The liquid discharge head according to claim 1, wherein the difference in the contact angles are different from each other is 10 degrees or more.

4. A liquid discharge head device comprising the liquid discharge head according to claim 1.

5. The liquid discharge head device according to claim 4, wherein the liquid is a liquid including a medicine used for lung inhalation.

* * * * *